United States Patent [19]

Fompeyrine et al.

[11] Patent Number: 4,933,497

[45] Date of Patent: Jun. 12, 1990

[54] PREPARATION OF HYDROXYBENZALDEHYDES BY HYDROCARBONYLATION OF HALOPHENOLS

[75] Inventors: Patricia Fompeyrine, Sainte Foy les Lyon; Francois Metz, Lyons, both of France

[73] Assignee: Rhone-Poulenc Chimie, Courbevoie, France

[21] Appl. No.: 379,556

[22] Filed: Jul. 13, 1989

[30] Foreign Application Priority Data

Jul. 13, 1988 [FR] France ............................ 88 09765

[51] Int. Cl.$^5$ ............................................ C07C 45/00
[52] U.S. Cl. .................................. 568/428; 568/41; 568/311; 560/51; 560/53; 549/70; 546/314; 558/415
[58] Field of Search .................. 568/428, 41, 311; 560/51; 549/70; 546/314; 558/415

[56] References Cited

U.S. PATENT DOCUMENTS

| | | | |
|---|---|---|---|
| 3,960,932 | 6/1976 | Heck | 568/428 |
| 4,536,344 | 8/1985 | Fiedler et al. | 568/428 |
| 4,605,749 | 8/1988 | Buchman et al. | 568/428 |

FOREIGN PATENT DOCUMENTS

| | | |
|---|---|---|
| 0244328 | 7/1977 | European Pat. Off. . |
| 0109606 | 5/1984 | European Pat. Off. . |
| 3242582 | 5/1984 | Fed. Rep. of Germany . |

*Primary Examiner*—Paul J. Killos
*Attorney, Agent, or Firm*—Burns, Doane, Swecker & Mathis

[57] ABSTRACT

Hydroxybenzaldehydes, e.g., vanillin, are prepared by hydrocarbonylating a corresponding halophenol, e.g., 4-bromo-2-methoxyphenol, in the presence of (a) a tertiary amine, (b) a catalyst based on a noble metal, and (c) a phosphine.

22 Claims, No Drawings

PREPARATION OF HYDROXYBENZALDEHYDES BY HYDROCARBONYLATION OF HALOPHENOLS

BACKGROUND OF THE INVENTION

1. Field of the Invention:

The present invention relates to the preparation of hydroxybenzaldehydes, and, more especially, to the preparation of hydroxybenzaldehydes by hydrocarbonylation of the corresponding halophenols.

2. Description of the Prior Art:

U.S. Pat. No. 3,960,932 describes a general process for the preparation of aldehydes by reacting aryl or vinyl halides, or halides of heterocyclic compounds, with a mixture of carbon monoxide and hydrogen in the presence of a tertiary amine and of a palladium catalyst consisting of a complex of a divalent palladium derivative with a phosphine, a phosphite or an arsine of the combination of a divalent palladium salt, or of finely divided metallic palladium, with a complexing agent of the phosphine, phosphite or arsine group. The aryl halides employed in the process described in U.S. Pat. No. 3,960,932 are phenyl or naphthyl bromides or iodides, unsubstituted or substituted by alkyl, alkoxy, nitrile or alkyl carboxylate groups.

European Patent EP No. 109,606 describes increasing the kinetics of the hydrocarbonylation reaction of the above process, by carrying out such reaction at pressures of 2 to 40 MPa (20 to 400 bar), at temperatures of 80° C. to 250° C., and by employing large amounts of phosphine or of phosphite (2 to $10^5$ times the molar quantity of catalyst).

It will of course be appreciated that these processes of the prior art do not relate to the hydrocarbonylation of halophenols.

SUMMARY OF THE INVENTION

Accordingly, a major object of the present invention is the provision of an improved process for the preparation of hydroxybenzaldehydes by reacting a halophenol with a carbon monoxide/hydrogen mixture, in the presence of (a) a tertiary amine, (b) a catalyst based on a noble metal, and (c) a phosphine.

Briefly, the present invention features a process for the preparation of a hydroxybenzaldehyde of the general formula (I):

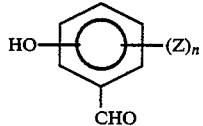

(I)

in which n is 0, 1 or 2; and Z is either an electron-donating group or an electron-attracting group, comprising reacting a halophenol of the general formula (II):

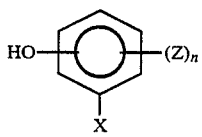

(II)

in which X is a bromine atom or an iodine atom, and Z and n are as defined above; with a carbon monoxide/hydrogen mixture, in the presence of a catalyst based on a noble metal, of a tertiary amine and of a phosphine, and wherein the tertiary amine is such that the $pK_a$ of its conjugate acid is greater than the $pK_a$ of the halophenol of formula (II) and the $pK_a$ of the phosphine is greater than or equal to 5.

DETAILED DESCRIPTION OF THE PREFERRED EMBODIMENTS OF THE INVENTION

More particularly according to the present invention, the $pK_a$ in water (generally at 25° C.) of the conjugate acid of the tertiary amine is reported in numerous tables which are contained in the literature.

The $pK_a$ in water of the phosphine is also reported in numerous tables which are contained in the literature.

The $pK_a$ of the halophenol of formula (II) is determined according to the IUPAC method Ezbg, entitled "Ionisation constants of organic acids in aqueous solutions" (published by Pergamon Press, 1979).

Thus, it has now unexpectedly and surprisingly been found that, in order to hydrocarbonylate a halophenol of formula (II) such as to prepare a hydroxybenzaldehyde of formula (I), on the one hand the $pK_a$ of the conjugate acid of the tertiary amine employed must be greater than or equal to that of the halophenol (II), and, on the other, the $pK_a$ of the phosphine must be greater than or equal to 5.

When the tertiary amine or the phosphine employed does not meet these conditions, a polymeric compound is essentially formed, but virtually no hydroxybenzaldehyde.

The starting material halophenols of formula (II) according to the present invention are especially those in which the symbol Z is a hydroxyl radical, a bromine atom, an iodine atom, an alkyl radical, an alkoxy radical, an alkyl or alkoxy radical substituted by one or more chlorine or fluorine atoms, a cycloalkyl radical, a phenyl radical, a cycloalkoxy radical, a phenoxy radical, an alkoxycarbonyl radical, a cycloalkoxycarbonyl radical, a phenoxycarbonyl radical, an alkyl carbonyloxy radical, a cycloalkylcarbonyloxy radical, a phenylcarbonyloxy radical, one of the above radicals substituted by one or more fluorine and/or chlorine atoms or nitrile groups, and the symbol X is a bromine atom or an iodine atom.

More preferably, in formulae (I) and (II), X is a bromine atom; and Z is a hydroxyl radical; a bromine atom; a linear or branched chain alkyl radical containing from 1 to 20 carbon atoms or such alkyl radical substituted by one or more fluorine and/or chlorine atoms, for example, methyl, ethyl, propyl, butyl, pentyl, hexyl, octyl, decyl, trifluoromethyl, difluorochloromethyl and trichloromethyl radicals; preferably a lower alkyl radical containing from 1 to 4 carbon atoms, or a lower alkyl radical substituted by 1 to 3 fluorine and/or chlorine atoms; a linear or branched chain alkoxy radical containing from 1 to 20 carbon atoms or such alkoxy radical substituted by one or more fluorine and/or chlorine atoms; preferably a lower alkoxy radical containing from 1 to 4 carbon atoms or a lower alkoxy radical substituted by 1 to 3 fluorine and/or chlorine atoms, such as, for example, methoxy, ethoxy, isopropoxy, difluorochloromethoxy, or trichloromethoxy radicals; a cyclopentyl, cyclohexyl or cyclooctyl radical; a phenyl radical or a phenyl radical substituted by 1 to 3 lower alkyl or alkoxy radicals, such as xylyl, tolyl, methoxy-phenyl or ethoxyphenyl radicals; an alkoxycarbonyl radical containing from 2 to 11 carbon atoms and preferably 2 to 5 carbon atoms, such as, for example, methoxycarbonyl, ethoxycarbonyl, propoxycarbonyl and butoxycarbonyl radicals; an alkoxycarbonylalkyl radical in which the alkoxycarbonyl moiety is as defined above and the alkyl moiety contains from 1 to 4 carbon atoms; a cyclopentyloxycarbonyl or cyclohexyloxycarbonyl radical; a phenoxycarbonyl or methylphenoxycarbonyl radical; an alkylcarbonyloxy radical containing from 2 to 11 carbon atoms and preferably 2 to 5 carbon atoms, such as, for example, acetoxy, propionyloxy or butyryloxy radicals; a cyclopentanoyloxy or cyclohexanoyloxy radical; or a benzoyloxy, methylbenzoyloxy or dimethylbenzoyloxy radical.

In formula (I), Z may also be an aldehyde group.

As specific examples of hydroxybenzaldehydes of formula (I) which can be prepared by the process according to the invention, particularly representative are 4-hydroxybenzaldehyde, 2-hydroxybenzaldehyde, vanillin (or 4-hydroxy3-methoxybenzaldehyde), 2-hydroxy-5-methoxybenzaldehyde, 2-hydroxy-3-methoxybenzaldehyde, 4-hydroxy-3-ethoxybenzaldehyde, 2-hydroxy-3-ethoxybenzaldehyde, 2-hydroxy-5-ethoxybenzaldehyde, 3,5-dimethoxy-4-hydroxybenzaldehyde, 3,4-dihydroxybenzaldehyde, 2,5-dihydroxybenzaldehyde, 2,3-dihydroxybenzaldehyde, 3,5-dibromo-4-hydroxybenzaldehyde, 3-bromo-4-hydroxybenzaldehyde and 3-formyl-4-hydroxybenzaldehyde.

As specific examples of halophenols of formula (II) which can be employed in the process of the invention, particularly representative are 4-bromophenol, 2-bromophenol, 4-bromo-2-methoxyphenol, 2-bromo-4-methoxyphenol, 6-bromo-2-methoxyphenol, 4-bromo-2-ethoxyphenol, 2-bromo-4-ethoxyphenol, 6-bromo-2-ethoxyphenol, 4-bromo-2,6-dimethoxyphenol, 4-bromo-1,2-dihydroxybenzene, 2-bromo-1,4-dihydroxybenzene, 3-bromo-1,2-dihydroxybenzene, 2,4-dibromophenol and 2,4,6-tribromophenol.

A finely divided noble metal of Group VIII of the Periodic Table of the elements, such as palladium, rhodium and iridium, or their inorganic or organic acid salts, may be employed as catalysts for carrying out the process according to the invention.

Palladium derivatives are very particularly suitable for the process of the invention.

As specific examples of the palladium derivatives, particularly representative are carboxylates such as, especially, palladium(II) acetates, propionates, butyrates, or benzoates, and palladous chloride.

It is also possible to employ complexes of inorganic or organic palladium salts with phosphine.

In the latter case, this complex is typically produced in situ between the palladium derivative and the phosphine present. However, said complex may also be prepared extemporaneously and may be introduced into the reaction mixture. An additional amount of free phosphine may or may not then be added.

The amount of catalyst, expressed in moles of metal atoms or in moles of metal derivative per mole of halophenol of formula (I), can vary over wide limits.

Thus, it may range from $10^{-5}$ to $10^{-1}$ mole/mole and preferably from $10^{-4}$ to $10^{-2}$ mole/mole.

The amount of phosphine which is free and/or in the form of a complex with the catalyst is such that the molar ratio phosphine/noble metal of the catalyst is at least equal to 2.

The phosphine/noble metal ratio may attain values as high as 10,000.

A phosphine/noble metal ratio ranging from 4 to 1,000 is typically highly suitable The phosphines whose $pK_a$ is equal to or greater than 5 are generally aliphatic, cycloaliphatic or arylaliphatic phosphines.

Mixed aliphatic and/or cycloaliphatic and/or arylaliphatic and/or aromatic phosphines may also be used.

These phosphines are especially those having the general formula (III):

in which the symbols $R_2$, $R_3$ and $R_4$, which may be identical or different, are each an alkyl radical containing from 1 to 12 carbon atoms; a cycloalkyl radical containing 5 to 6 carbon atoms; a cycloalkyl radical containing 5 to 6 carbon atoms, substituted by one or more alkyl radicals containing from 1 to 4 carbon atoms, or alkoxy radicals containing from 1 to 4 carbon atoms; a phenylalkyl radical in which the aliphatic moiety contains from 1 to 6 carbon atoms; with the proviso that one or two of the radicals $R_2$, $R_3$ and $R_4$ may be a phenyl radical or a phenyl radical substituted by one or more alkyl radicals containing from 1 to 4 carbon atoms or alkoxy radicals containing from 1 to 4 carbon atoms.

Exemplary of such phosphines are tricyclohexylphosphine, trimethylphosphine, triethylphosphine, tri-n-butylphosphine, triisobutylphosphine, tri-tert-butylphosphine, tribenzylphosphine, dicyclohexylphenylphosphine, dimethylphenylphosphine, diethylphenylphosphine and di-tertbutylphenylphosphine.

The tertiary amine employed in the process of the invention may be an amine of the general formula (IV):

in which the radicals $R_1$, which may be identical or different, are hydrocarbon radicals containing from 1 to 20 carbon atoms, such as alkyl, cycloalkyl, aryl or heterocyclic radicals; with the proviso that two of the radicals $R_1$ may together form, with the nitrogen atom, a heterocyclic ring containing from 4 to 6 carbon atoms.

More preferably, the symbols $R_1$ are alkyl radicals containing from 1 to 10 carbon atoms and preferably from 1 to 4 carbon atoms, or a cyclopentyl or cyclohexyl radical or a pyridyl radical; and the two radicals $R_1$ may form, together with the nitrogen atom, a piperidine or pyrrolidine ring.

Exemplary of such amines are triethylamine, tri-n-propylamine, tri-n-butylamine, methyldibutylamine, methyldicyclohexylamine, ethyldiisopropylamine, N,N-diethylcyclohexylamine, 4-dimethylaminopyridine, N-methylpiperidine, N-ethylpiperidine, N-n-butylpiperidine, 1,2-dimethylpiperidine, N-methylpyrrolidine and 1,2-dimethylpyrrolidine.

When a halophenol is used, such as 2-bromophenol, 4-bromophenol, 4-bromo-2-methoxyphenol or 4-bromo-2-ethoxyphenol, which result in the preparation of extremely commercially important hydroxybenzaldehydes and the $pK_a$ (at 25° C.) of which is 9.5 in the case of 4-bromophenol and 4-bromo-2-methoxyphenol, and close to this value in the case of 4-bromo-2-ethoxyphenol, and 8.55 in the case of 2-bromophenol, tertiary amines of formula (IV) such as triethylamine, which have a $pK_a$ of their conjugate acid greater than 9.5, are suitable.

The amount of tertiary amine employed must be sufficient to neutralize the hydracid released during the reaction.

In addition, the concentration of tertiary amine in the mixture must be at least 2 moles per liter during the reaction period.

There is no critical upper limit to the amount of tertiary amine. Therefore, it may be employed in a large excess relative to the amount theoretically required to neutralize the hydracid formed.

To maintain the tertiary amine concentration at least equal to the limiting values indicated during the reaction period, the amount of amine introduced must be calculated such that its concentration is at least equal to these values when the reaction is complete. An additional amount of tertiary amine may also be added in consideration of the progress of the reaction, in order to compensate for the amount of amine consumed by the neutralization of the hydracid.

$CO/H_2$ mixtures having varying molar ratios of both gases may be employed. The $CO/H_2$ molar ratio typically ranges from 0.1 to 10.

The pressure at which the process is carried out may vary quite widely. It typically ranges from 0.1 to 30 MPa (1 to 300 bar) and preferably from 1 to 15 MPa (10 to 150 bar).

The process according to the invention is conducted in liquid phase.

A solvent which is inert under the conditions of the hydrocarbonylation reaction may also be used. Thus, it is possible to use saturated aliphatic or cycloaliphatic hydrocarbons such as hexane or cyclohexane, or aromatic hydrocarbons such as benzene, toluene and xylenes; esters such as methyl benzoate, methyl terephthalate, methyl adipate and dibutyl phthalate; polyol esters or ethers such as tetraethylene glycol diacetate; and cyclic ethers such as tetrahydrofuran dioxane.

The concentration of the halophenol of formula (II) in the solvent may vary over very wide limits, up to saturation under the operating conditions selected. It is generally of no economic interest to use less than 5% by weight of halophenol per volume of solvent.

The concentration by weight of halophenol per volume of solvent typically ranges from 5% to 50%, and preferably from 10% to 40%.

In practice, the process according to the invention may be carried out by introducing into an inert autoclave the halophenol of formula (II), the tertiary amine, the catalyst, the phosphine and the solvent and then, after the typical purges, by charging the autoclave with a suitable pressure of a $CO/H_2$ mixture. The contents of the autoclave are then heated to the appropriate temperature, under stirring, until the absorption ceases. The pressure in the autoclave can be maintained constant throughout the reaction period by virtue of a reserve of gas mixture, which is introduced at the selected pressure.

When the reaction is complete, the autoclave is cooled and degassed. The reaction mixture is recovered.

A very simple recovery technique entails adding an aqueous solution of an alkali metal hydroxide to the reaction mixture.

After stirring and permitting the mixture, an aqueous phase and an organic phase are thus obtained. The organic phase essentially contains the catalyst, the phosphine and at least a part of the tertiary amine. This organic solution can be easily recycled to a new hydrocarbonylation reaction, after addition of a new charge of the halophenol and, if desired, of make-up tertiary amine.

The aqueous phase essentially contains the hydroxybenzaldehyde formed, in the form of alkali metal phenate, as well as any byproducts and any unconverted halophenol, also in the form of alkali metal derivatives thereof.

A simple acidification and either a recrystallization, when the product is solid, or a distillation, when the product is liquid, enable the pure hydroxybenzaldehyde to be recovered.

The process may be carried out noncontinuously, or continuously as indicated above, the catalyst, the phosphine and the tertiary amine being recycled.

In order to further illustrate the present invention and the advantages thereof, the following specific examples are given, it being understood that same are intended only as illustrative and in nowise limitative.

EXAMPLES 1 and 2 and COMPARATIVE EXAMPLE A

The following materials were charged into a 125-cm³ autoclave made of an alloy marketed as Hastelloy B2, fitted with a heating device, and under stirring:
(i) 10.15 g (50 mmol) of 4-bromo-2-methoxyphenol;
(ii) 0.22 g (1 mmol) of palladium diacetate;
(iii) 5 mmol of a phosphine (indicated in the Table I below);
(iv) 110 mmol of 4-dimethylaminopyridine; and
(v) 17.5 cm³ of toluene.

| | |
|---|---|
| $pK_a$ of 4-bromo-2-methoxyphenyl: | 9.5. |
| $pK_a$ of the conjugate acid of the amine: | 9.55. |

The autoclave was closed and purged with an equimolar mixture of CO and $H_2$.

This $CO/H_2$ mixture was then charged at a pressure of 0.1 MPa (1 bar); the contents of the autoclave were heated under stirring to 100° C.; the $CO/H_2$ pressure was adjusted to 3 MPa (30 bar), and the temperature was then increased to 150° C.

The temperature was maintained at 150° C. and the pressure at 3 MPa until the absorption of the $CO/H_2$ mixture had ceased.

The autoclave was then cooled and degassed.

After a sample was removed for determination by liquid chromatography, 40 cm³ of an aqueous sodium hydroxide solution (6 g of sodium hydroxide) were added to the reaction mixture and the autoclave was stirred at ambient temperature for 1 hour.

The aqueous phase was isolated by phase separation, was acidified with HCl to pH 1 and was extracted with three 100 cm³ portions of ethyl ether.

The ether solution obtained was treated with two 50 cm³ portions of an aqueous 20% strength solution of sodium hydrogen carbonate.

The ether solution was then separated and the ether was evaporated off.

The resulting brown solid was recrystallized from toluene and then from water, to produce pure vanillin.

Table I below reports, for each example, the data concerning phosphine, time, the degree of conversion (DC %) of 4-bromo-2-methoxyphenol (BMPH), the yield (CY %) of 4-hydroxy-3-methoxybenzaldehyde (vanillin) (HMBZ) relative to the 4-bromo-2-methoxyphenol converted, and the % CYs of quaiacol and of any 4-hydroxy-3-benzoic acid formed.

The difference between 100% and the total of the CYs indicated above corresponds to the formation of a polymeric compound of the structure:

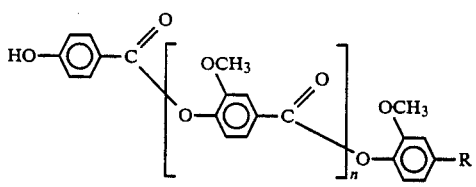

n being equal to or greater than 1 and R being CHO, H or Br.

It will be appreciated that when the $pK_a$ of the phosphine was lower than 5, the yield of aldehyde was low (Comparative Example A).

TABLE I

| Examples | Phosphine | $pK_a$* | Time | % DC of BMPH** | % CY of HMBZ** | % CY of gaiacol | % CY of HMBQ** |
|---|---|---|---|---|---|---|---|
| Example 1 | tricyclohexyl-phosphine | 9.7 | 2 h, 40 min | 96 | 60.5 | 9.6 | 0 |
| Example 2 | triethyl-phosphine | 8.69 | 5 h, 30 min | 73 | 37 | 45 | 0 |
| Comparative Example A | triphenyl-phosphine | 2.74 | 20 min | 100 | 8 | 2 | 0.2 |

*$pK_a$ of the phosphine
**BMPH = 4-bromo-2-methoxyphenol
HMBZ = 4-hydroxy-3-methoxy-benzaldehyde
HMBQ = 4-hydroxy-3-methoxy-benzoic acid

EXAMPLES 3 to 5 and COMPARATIVE EXAMPLE B:

The following materials were charged into a 125 cm³ autoclave made of an alloy marketed as Hastelloy B2, fitted with a heating device, and under stirring:
(i) 10.15 g (50 mmol) of 4-bromo-2-methoxyphenol;
(ii) 0.22 g (1 mmol) of palladium diacetate;
(iii) 5 mmol of a phosphine (indicated in the Table II below);
(iv) 110 mmol of triethylamine; and
(v) 17.5 cm³ of toluene.

| | |
|---|---|
| $pK_a$ of 4-bromo-2-methoxyphenol: | 9.5. |
| $pK_a$ of the conjugate acid of the amine: | 11.1. |

The autoclave was closed and purged with an equimolar mixture of CO and of $H_2$.

This $CO/H_2$ mixture was then charged at a pressure of 0.1 MPa (1 bar); the contents of the autoclave were heated under stirring to 100.C; the $CO/H_2$ pressure was adjusted to 3 MPa (30 bar), and the temperature was then increased to 150° C.

The temperature was maintained at 150° C. and the pressure at 3 MPa until the absorption of the $CO/H_2$ mixture had ceased.

The autoclave was then cooled and degassed.

A sample was withdrawn for determination by liquid chromatography. The treatment was that described in the case of Examples 1 and 2.

The Table II below reports, for each example, the data concerning the phosphine employed, the time, the degree of conversion (DC %) of 4-bromo-2-methoxyphenol (BMPH), the yield (CY %) of 4-hydroxy-3-methoxybenzaldehyde (vanillin) (HMBZ) relative to the 4-bromo-2-methoxyphenol converted, and the % CYs of quaiacol and of any 4-hydroxy-3-methoxybenzoic acid formed.

The difference between 100% and the total of the CYs indicated above corresponds to the polymeric compound shown in Examples 1 and 2.

It will be appreciated that when the $pK_a$ of the phosphine was lower than 5, the yield of aldehyde was zero (comparative Example B).

TABLE II

| Examples | Phosphine | $pK_a$* | Time | % DC of BMPH** | % CY of HMBZ** | % CY of gaiacol | % CY of HMBQ** |
|---|---|---|---|---|---|---|---|
| Example 3 | tricyclohexyl-phosphine | 9.7 | 1 h, 50 min | 98 | 71 | 13 | 0.1 |
| Example 4 | triethyl-phosphine | 8.69 | 5 h, 40 min | 71 | 42 | 46.5 | 0 |
| Example 5 | tribenzyl-phosphine | 6.0 | 3 h, 25 min | 84 | 69 | 28.5 | 0 |
| Comparative Example B | triphenyl-phosphine | 2.74 | 20 min | 100 | 0 | 0 | 0 |

*$pK_a$ of the phosphine
**BMPH = 4-bromo-2-methoxyphenol
HMBZ = 4-hydroxy-3-methoxy-benzaldehyde (vanillin)
HMBQ = 4-hydroxy-3-methoxy-benzoic acid

EXAMPLE 6 and COMPARATIVE EXAMPLE C:

The following materials were charged into a 125 cm³ autoclave made of an alloy marketed as Hastelloy B2, fitted with a heating device, and under stirring:
(i) 8.65 g (50 mmol) of 2-bromophenol;
(ii) 0.22 g (1 mmol) of palladium diacetate;
(iii) 5 mmol of a phosphine (indicated in Table III below);
(iv) 110 mmol of triethylamine; and
(v) 17.5 cm³ of toluene.

| | |
|---|---|
| $pK_a$ of 2-bromophenol: | 8.55. |
| $pK_a$ of the conjugate acid of the amine: | 11.1. |

The autoclave was closed and purged with an equimolar mixture of CO and of $H_2$.

This $CO/H_2$ mixture was then charged at a pressure of 0.1 MPa (1 bar); the contents of the autoclave were heated under stirring to 100.C; the $CO/H_2$ pressure was adjusted to 3 MPa (30 bar), and the temperature was then increased to The temperature was maintained at 150° C. and the pressure at 3 MPa until the absorption of the $CO/H_2$ mixture had ceased.

The autoclave was then cooled and degassed.

A sample was taken for determination by liquid chromatography. The treatment was that described in the case of Examples 1 and 2.

The Table III below reports, for each example, the data concerning the phosphine employed, the time, the degree of conversion (DC %) of 2-bromophenol (2BPH), the yield (CY %) of 2-hydroxybenzaldehyde or salicylaldehyde (SAL) relative to the 2-bromophenol converted, and the % CYs of phenol and of any salicylic acid (SAC) formed.

The difference between 100% and the total of the CYs indicated above corresponds to a polymeric compound having a structure of the type as that shown in Examples 1 and 2.

It will be appreciated that when the $pK_a$ of the phosphine pas lower than 5, the yield of aldehyde was low (Comparative Example C).

The autoclave was closed and purged with an equimolar mixture of CO and of $H_2$.

This $CO/H_2$ mixture was then charged at a pressure of 0.1 MPa (1 bar); the contents of the autoclave were heated under stirring to 100.C; the $CO/H_2$ pressure was adjusted to 3 MPa (30 bar), and the temperature was then increased to 150° C.

The temperature was maintained at 150° C. and the pressure at 3 MPa until the absorption of the $CO/H_2$ mixture had ceased.

The autoclave was then cooled and degassed.

A sample was withdrawn for determination by liquid chromatography. The treatment was that described in the case of Examples 1 and 2.

The Table IV below reports, for each example, the data concerning the phosphine employed, the time, the degree of conversion (DC %) of 4-bromophenol (4BPH), the yield (CY %) of 4-hydroxybenzaldehyde (4HBZ) relative to the 4-bromophenol converted, and the % CYs of phenol and of any 4-hydroxybenzoic acid (4HBZ) formed.

The difference between 100% and the total of the CYs indicated above corresponds to a polymeric compound having a structure of the type as that shown in Examples 1 and 2.

It will be appreciated that when the $pK_a$ of the phosphine was lower than 5, the yield of aldehyde was very low (Comparative Example D).

TABLE III

| Examples | Phosphine | $pK_a$* | Time | % DC of 2BPH** | % CY of SAL** | % CY of phenol | % CY of SAC** |
|---|---|---|---|---|---|---|---|
| Example 6 | tricyclohexyl-phosphine | 9.7 | 2 h, 30 min | 93 | 53 | 14 | 3 |
| Comparative Example C | triphenyl-phosphine | 2.74 | 2 h, 30 min | 100 | 6 | 2 | 7 |

*$pK_a$ of the phosphine
**2BPH = 2-bromophenol
SAL = salicylaldehyde
SAC = salicylic acid

TABLE IV

| Examples | Phosphine | $pK_a$* | Time | % DC of 4BPH** | % CY of 4HBZ** | % CY of phenol | % CY of 4HBQ** |
|---|---|---|---|---|---|---|---|
| Example 7 | tricyclohexyl-phosphine | 9.7 | 20 min | 92 | 58 | 9.8 | 2.2 |
| Comparative Example D | triphenyl-phosphine | 2.74 | 20 min | 99 | 2 | 2 | 0 |

*$pK_a$ of the phosphine
**4BPH = 4-bromophenol
4HBZ = 4-hydroxybenzaldehyde
4HBQ = 4-hydroxybenzoic acid EXAMPLE 7 and COMPARATIVE EXAMPLE D:

The following materials were charged into a 125 $cm^3$ autoclave made of an alloy marketed as Hastelloy B2, fitted with a heating device, and under stirring:

(i) 8.65 g (50 mmol) of 4-bromophenol;
(ii) 0.22 g (1 mmol) of palladium diacetate;
(iii) 5 mmol of a phosphine (indicated in Table IV below);
(iv) 110 mmol of triethylamine; and
(v) 17.5 $cm^3$ of toluene.

| | |
|---|---|
| $pK_a$ of 4-bromophenol: | 9.5. |
| $pK_a$ of the conjugate acid of the amine: | 11.1. |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

WHAT IS CLAIMED IS:

1. A process for the preparation of a hydroxybenzaldehyde of the general formula (I):

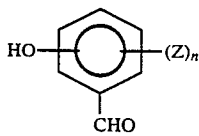

in which n is 0, 1 or 2, and Z is an electron-donating group or an electron-attracting group, comprising reacting a halophenol of the general formula (II):

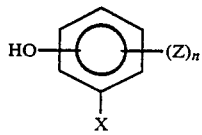

in which X is a bromine atom or an iodine atom, and Z and n are as defined above, with a carbon monoxide/hydrogen mixture, in the presence of a catalyst based on a noble metal, a tertiary amine and a phosphine, and wherein the tertiary amine is such that the $pK_a$ of its conjugate acid is greater than the $pK_a$ of the halophenol of formula (II) and the $pK_a$ of the phosphine is greater than or equal to 5.

2. The process as defined by claim 1, wherein said halophenol of formula (II), the symbol Z is a hydroxyl radical, a bromine atom, an iodine atom, an alkyl radical, an alkoxy radical, an alkyl or alkoxy radical substituted by one or more chlorine or fluorine atoms, a cycloalkyl radical, a phenyl radical, a cycloalkoxy radical, a phenoxy radical, an alkoxycarbonyl radical, a cycloalkoxycarbonyl radical, a phenoxycarbonyl radical, an alkylcarbonyloxy radical, a cycloalkylcarbonyloxy radical, a phenylcarbonyloxy radical, one of the above radicals substituted by one or more fluorine and/or chlorine atoms or nitrile groups, and the symbol X is a bromine atom or an iodine atom.

3. The process as defined by claim 1, wherein said halophenol of formula (II), X is a bromine atom; and Z is a hydroxyl radical; a bromine atom; a linear or branched chain alkyl radical containing from 1 to 20 carbon atoms or such alkyl radical substituted by one or more fluorine and/or chlorine atoms; a linear or branched chain alkoxy radical containing from 1 to 20 carbon atoms or such alkoxy radical substituted by one or more fluorine and/or chlorine atoms; a phenyl radical or a phenyl radical substituted by 1 to 3 lower alkyl or alkoxy radicals; an alkoxycarbonyl radical containing from 2 to 11 carbon atoms; an alkoxycarbonylalkyl radical in which the alkoxycarbonyl moiety is as defined above and the alkyl moiety contains 1 to 4 carbon atoms; a cyclopentyloxycarbonyl or cyclohexyloxycarbonyl radical; a phenoxycarbonyl or methylphenoxycarbonyl radical, an alkylcarbonyloxy radical containing from 2 to 11 carbon atoms; a cyclopentanoyloxy or cyclohexanoyloxy radical; or a benzoyloxy, methylbenzoyloxy or dimethylbenzoyloxy radical.

4. The process as defined by claim 1, said halophenol of formula (II) comprising 4-bromophenol, 2-bromophenol, 4-bromo-2-methoxyphenol, 2-bromo-4-methoxyphenol, 6-bromo-2-methoxyphenol, 4-bromo-2-ethoxyphenol, 2-bromo-4-ethoxyphenol, 6-bromo-2-ethoxyphenol, 4-bromo-2,6-dimethoxyphenol, 4-bromo-1,2-dihydroxybenzene, 2-bromo-1,4-dihydroxybenzene, 3-bromo-1,2-dihydroxybenzene, 2,4-dibromophenol or 2,4,6-tribromophenol.

5. The process as defined by claim 1, said catalyst comprising a finely divided noble metal of Group VIII of the Periodic Table.

6. The process as defined by claim 5, said catalyst comprising palladium, rhodium or iridium, or an inorganic or organic acid salt thereof.

7. The process as defined by claim 6, said catalyst comprising a palladium carboxylate or palladous chloride.

8. The process as defined by claim 1, wherein the amount of catalyst, expressed in moles of metal atoms or in moles of metal derivative per mole of halophenol of formula (I), ranges from $10^{-5}$ to $10^{-1}$ mole/mole.

9. The process as defined by claim 1, said phosphine comprising an aliphatic phosphine, a cycloaliphatic phosphine, an arylaliphatic phosphine, or a mixed aliphatic and/or cycloaliphatic and/or arylaliphatic and/or aromatic phosphine.

10. The process as defined by claim 9, said phosphine having the general formula (III):

in which the symbols $R_2$, $R_3$ and $R_4$, which may be identical or different, are each an alkyl radical containing from 1 to 12 carbon atoms; a cycloalkyl radical containing 5 or 6 carbon atoms; a cycloalkyl radical containing 5 or 6 carbon atoms, substituted by one or more alkyl radicals containing 1 to 4 carbon atoms, or alkoxy radicals containing 1 to 4 carbon atoms; a phenylalkyl radical in which the aliphatic moiety contains from 1 to 6 carbon atoms; with the proviso that one or two of the radicals $R_2$, $R_3$ and $R_4$ may be a phenyl radical or a phenyl radical substituted by one or more alkyl radicals containing 1 to 4 carbon atoms or alkoxy radicals containing I6 1 to 4 carbon atoms.

11. The process as defined by claim 10, said phosphine comprising tricyclohexylphosphine, trimethylphosphine, triethylphosphine, tri-n-butylphosphine, triisobutylphosphine, tri-tert-butylphosphine, tribenzylphosphine, dicyclohexylphenylphosphine, dimethylphenylphosphine, diethylphenylphosphine or di-tert-butylphenylphosphine.

12. The process as defined by claim 1, wherein the amount of phosphine is such that the molar ratio phosphine/noble metal of the catalyst ranges from 2 to 10,000.

13. The process as defined by claim 12, said molar ratio ranging from 4 to 1,000.

14. The process as defined by claim 1, said tertiary amine having the general formula (IV):

in which the radicals $R_1$, which may be identical or different, are each a hydrocarbon radical containing from 1 to 20 carbon atoms, or a heterocyclic radical; with the proviso that two of the radicals $R_1$ may together form, with the nitrogen atom, a heterocyclic ring containing 4 to 6 carbon atoms.

15. The process as defined by claim 14, wherein said tertiary amine of general formula (IV), the symbols $R_1$ are each an alkyl radical containing from 1 to 10 carbon atoms, or a cyclopentyl, cyclohexyl or pyridyl radical;

with the proviso that two of the radicals $R_1$ may together form, with the nitrogen atom, a piperidine or pyrrolidine ring.

16. The process as defined by claim 14, said tertiary amine comprising triethylamine, tri-n-propylamine, tri-n-butylamine, methyldibutylamine, methyldicyclohexylamine, ethyldiisopropylamine, N,N-diethylcyclohexylamine, 4-dimethylaminopyridine, N-methylpiperidine, N-ethylpiperidine, N-n-butylpiperidine, 1,2-dimethylpiperidine, N-methylpyrrolidine or 1,2-dimethylpyrrolidine.

17. The process as defined by claim 1, wherein the amount of tertiary amine is sufficient to neutralize the hydracid released during the reaction and that the concentration of tertiary amine in the mixture is at least equal to 2 moles per liter over the course of the reaction.

18. The process as defined by claim 1, carried out at a pressure of from 0.1 to 30 MPa (1 to 300 bar).

19. The process as defined by claim 1, carried out in an inert organic solvent.

20. The process as defined by claim 19, said inert organic solvent comprising a saturated aliphatic or cycloaliphatic hydrocarbon, an aromatic hydrocarbon, an ester, a polyol ester or ether, or a cyclic ether.

21. The process as defined by claim 19, wherein the concentration of the halophenol of formula (I), expressed as weight of halophenol per volume of solvent, ranges from 5% to 50%.

22. The process as defined by claim 1, further comprising treating the mixture of complete reaction with an aqueous solution of an alkali metal hydroxide.

* * * * *